United States Patent [19]
Galey et al.

[11] Patent Number: 5,968,487
[45] Date of Patent: Oct. 19, 1999

[54] DERIVATIVE OF KOJIC ACID AND ITS USE AS A DEPIGMENTING AGENT

[75] Inventors: Jean-Baptiste Galey, Aulnay-Sous-Bois; Patrick Pichaud, Velizy, both of France

[73] Assignee: L'Oreal, Paris, France

[21] Appl. No.: 08/897,058

[22] Filed: Jul. 18, 1997

[30] Foreign Application Priority Data

Jul. 18, 1996 [FR] France ................................ 96-09011

[51] Int. Cl.$^6$ ...................................................... A61K 7/48
[52] U.S. Cl. ............................ 424/62; 424/43; 424/450; 424/489; 424/DIG. 5; 514/365; 514/844; 514/846; 514/937; 514/944; 514/945; 548/201
[58] Field of Search ................................ 424/62, 489, 43, 424/450, DIG. 5; 514/365, 844, 846, 937, 944, 945; 548/201

[56] References Cited

U.S. PATENT DOCUMENTS 5,208,249  5/1993  Rowe et al. ............................ 514/369

FOREIGN PATENT DOCUMENTS 0 650 725 A1   5/1995   European Pat. Off. .
2 175 584     12/1986   Germany .

OTHER PUBLICATIONS

Chemical Abstracts, vol. 121, No. 10, Sep. 5, 1994, pp. 589 & JP 06 133 773 A (abstract only).

*Primary Examiner*—Jyothsna Venkat
*Attorney, Agent, or Firm*—Oblon, Spivak, McClelland, Maier & Neustadt, P.C.

[57] ABSTRACT

The invention relates to a novel derivative of kojic acid of formula (I) and to its use, in a composition for topical application as a depigmenting and/or bleaching agent for skin:

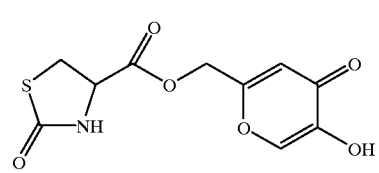

(I)

The invention also relates to a process for depigmenting and/or bleaching skin, which includes applying to the skin a composition that contains 5-hydroxy-4-oxo-4H-pyran-2-ylmethyl 2-oxothiazolidine-4-carboxylate of formula (I) or a pharmaceutically acceptable salt thereof.

11 Claims, No Drawings

DERIVATIVE OF KOJIC ACID AND ITS USE AS A DEPIGMENTING AGENT

BACKGROUND OF THE INVENTION

1. Field of the Invention

The present invention relates to a novel derivative of kojic acid and to its use in a composition for topical application as a depigmenting and/or bleaching agent for skin.

2. Discussion of the Background

Skin color depends on different factors such as the seasons of the year, race, and sex. Skin color is mainly determined by the concentration of melanin produced by the melanocytes. In addition, at different periods in life, certain individuals develop dark and/or colored blemishes on the skin and more especially on the hands, making the skin non-uniform in color. These blemishes may also arise due to a high concentration of melanin in the keratinocytes at the skin surface.

For several years, it has been sought to decrease and/or slow down the production of melanin in order to depigment or bleach the skin by acting on one or more of the points in the intracellular biochemical synthesis of melanin. To achieve this end, various compounds have been tested and used as depigmenting or bleaching agents for human skin.

The mechanism of skin pigmentation, i.e., forming melanin, is particularly complex and is believed to involve the following steps:

Tyrosine→Dopa→Dopaquinone→Dopachrome→Melanin

Tyrosinase is the essential enzyme involved in the above reaction sequence. In particular, tyrosinase is believed to catalyze the reaction for converting tyrosine into dopa (dihydroxyphenylalanine) and the reaction for converting dopa into dopaquinone. Tyrosinase is believed to act only when it is in the mature state, under the action of certain biological factors.

Generally, a substance is recognized as being depigmenting if it acts directly on the viability of the epidermal melanocytes in which melanogenesis takes place and/or if it interferes with one of the steps in the biosynthesis of melanin either by inhibiting one of the enzymes involved in melanogenesis or by becoming intercalated as a structural analogue of one of the chemical compounds in the melanin synthesis chain, described above, whereby the chain is effectively blocked thus ensuring depigmentation.

The substances most commonly used as depigmenting agents in compositions are, for example, vitamin C, vitamin C derivatives, vitamin E derivatives, arbutin, hydroquinone, kojic acid, placental derivatives, and glutathione and its derivatives.

The above compounds are believed to act on the synthesis and/or activity of tyrosinase, the enzyme involved in the synthesis of melanin, or to reduce the amount of melanin formed, or, alternatively, to stimulate the removal of melanin via the keratinocytes. Unfortunately, the compounds are either toxic, in the case of hydroquinone, or unstable in solution, in the case of vitamin C and kojic acid, and are therefore difficult to manufacture, or else they have unpleasant sulfurous odors, for example, glutathione. Consequently, use of the above compounds is limited.

Thus, there is a need for a novel skin-bleaching agent which is at least as effective as the conventional agents but does not have their disadvantages, i.e., one that is stable in a composition, is non-toxic when applied to the skin, and has no unpleasant odor.

SUMMARY OF THE INVENTION

One object of the invention, therefore, is to provide a novel compound that inhibits the synthesis of melanin and is thus capable of acting on skin pigmentation and blemishes without any risk of toxicity.

Another object of the invention is to provide a novel compound that is effective in bleaching and/or depigmenting skin.

Another object of the invention is to provide a skin bleaching and/or depigmenting composition that is stable, non-toxic when applied to skin, and has no unpleasant odor.

Another object of the invention is to provide a cosmetic composition for depigmenting and/or bleaching skin that can be safely applied to skin.

Another object of the invention is to provide a dermatological and/or medicinal composition for depigmenting and/or bleaching skin.

Another object of the invention is to provide a safe, effective cosmetic and/or dermatological treatment process for bleaching and/or depigmenting skin.

These and other objects of the invention have been achieved by a novel compound, 5-hydroxy-4-oxo-4H-pyran-2-ylmethyl 2-oxothiazolidine-4-carboxylate of formula (I):

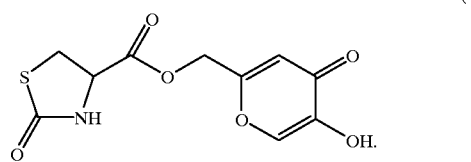

The first embodiment of the invention relates to a 5-hydroxy-4-oxo-4H-pyran-2-ylmethyl 2-oxothiazolidine-4-carboxylate compound having the formula (I):

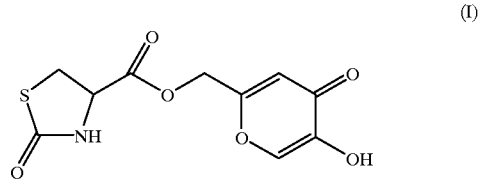

The second embodiment of the invention relates to a composition containing a skin depigmenting effective amount of a 5-hydroxy-4-oxo-4H-pyran-2-ylmethyl 2-oxothiazolidine-4-carboxylate compound having the formula (I):

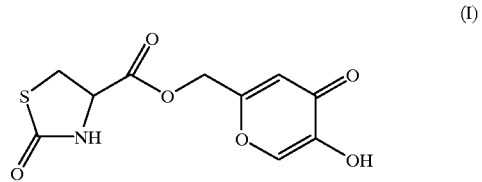

or pharmaceutically acceptable salts thereof.

The third embodiment of the invention relates to a composition containing a skin depigmenting effective amount of the product of mixing a 5-hydroxy-4-oxo-4H-pyran-2-ylmethyl 2-oxothiazolidine-4-carboxylate compound having the formula (I):

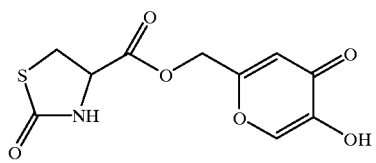

or a pharmaceutically acceptable salt thereof; with a cosmetic, dermatological, or medicinal composition; and allowing it to react.

The fourth embodiment of the invention relates to a method of depigmenting skin, which includes:

applying, to human skin, a composition containing a skin depigmenting effective amount of a 5-hydroxy-4-oxo-4H-pyran-2-ylmethyl 2-oxothiazolidine-4-carboxylate compound having the formula (I):

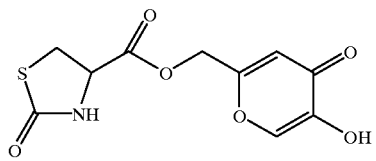

or a pharmaceutically acceptable salt thereof.

The fifth embodiment of the invention relates to a method of inhibiting the production of melanin, which includes:

contacting melanocytes with a melanin production inhibiting effective amount of a 5-hydroxy-4-oxo-4H-pyran-2-ylmethyl 2-oxothiazolidine-4-carboxylate compound having the formula (I):

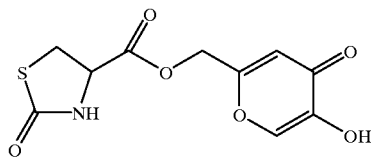

or a pharmaceutically acceptable salt thereof

The Applicants have found that the novel compound shows improved skin depigmenting activity over that of conventional agents, and, particularly, kojic acid. In addition, the novel compound is stable, non-toxic, and has no unpleasant odor.

BRIEF DESCRIPTION OF THE PREFERRED EMBODIMENTS

Various other objects, features and attendant advantages of the present invention will be more fully appreciated as the same becomes better understood from the following detailed description of the preferred embodiments, which are not intended to be limiting thereof.

Preferably the invention relates to depigmenting and/or bleaching human skin.

Preferably, the process for preparing the kojic acid derivative of the invention includes esterifying the alcohol function of kojic acid with L-2-oxothiazolidine-4-carboxylic acid.

More particularly, the process includes preparing the bromo derivative of kojic acid and reacting this bromo derivative with L-2-oxothiazolidine-4-carboxylic acid.

The most preferable process includes:

mixing kojic acid, dissolved in acidic medium, with hydrobromic acid, heating the reaction mixture, cooling it and filtering it;

reacting the bromo derivative obtained with L-2-oxothiazolidine-4-carboxylic acid, in the presence of potassium carbonate;

heating the reaction mixture, cooling it and filtering it.

Most especially preferably the process for the manufacture of the kojic acid derivative of the invention follows the general scheme below:

First Step:

During the first step, kojic acid dissolved in sulphuric acid is reacted with hydrobromic acid according to the following equation:

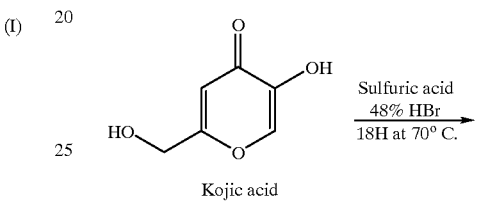

Kojic acid

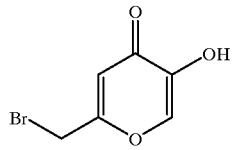

5 g of kojic acid are dissolved in 15 ml of concentrated sulphuric acid. The exothermicity is controlled with a bath of water and ice. 20 ml of 48 % hydrobromic acid are added slowly. Evolution of an orange gas is observed. The mixture is then heated at 70° C. for 18 hours. The reaction is left to cool to about 40° C. and the medium is then poured into 110 g of a mixture of water and ice. A slightly brown product precipitates out. After stirring for 1 hour, the mixture is filtered through a sinter funnel and the solid obtained is washed with 10 ml of water. The product is dried in a desiccator under vacuum at 50° C. 6.7 g of a light brown solid are recovered. Yield$_{crude}$=93%.

The product is used without further purification for the following reaction, or may be purified by reslurrying in hot water (TLC: Rf=0.7 in the eluent system CH$_2$Cl$_2$ (9)/MeOH (1)).

The $^1$H NMR of the product obtained is in accordance with the expected structure.

Second Step:

In the second step, the product obtained in the first step is reacted with L-2-oxothiazolidine-4-carboxylic acid according to the following equation:

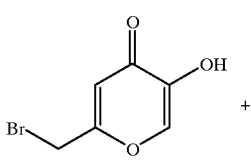

+

-continued

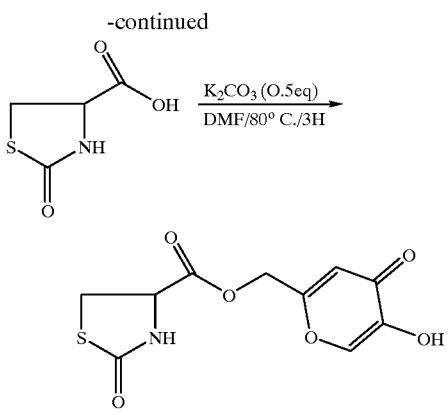

20.4 mmol of 2-oxothiazolidine-4-carboxylic acid in 10 ml of anhydrous DMF (rapid dissolution) are introduced into a 50 ml reactor. 0.5 eq of $K_2CO_3$ is added and the mixture is heated at 80° C. for 20 minutes. 21.4 mmol of the bromo derivative isolated in the first step are then added. The salts precipitate out rapidly. After reacting for 3 hours, the mixture is filtered in order to remove the insoluble material and is evaporated to dryness. A gum is obtained. This gum is taken up in 100 ml of water and is left stirring for 1 hour and then filtered through a sinter funnel. The solid obtained is dried in a desiccator under vacuum at 50° C.

Mass obtained: 2 g. Yield$_{crude}$=36%.

The solid is reslurried in 25 ml of hot methanol. The mixture is refluxed for 1 hour and then allowed to cool to room temperature. It is filtered through a sinter funnel; the solid is then dried in a desiccator under vacuum at 50° C. Mass recovered: 0.8 g. Yield=15%.

The $^1H$ NMR of the product obtained is in accordance with the expected structure.

The elemental analysis of the product obtained is as follows:

|  | C | H | N | O | S |
|---|---|---|---|---|---|
| THEORETICAL | 44.28% | 3.34% | 5.16% | 35.39% | 11.82% |
| FOUND | 44.24% | 3.39% | 5.17% | 34.53% | 11.32% |

As indicated above, the process may optionally be completed by a step of preparing a salt, for example, a pharmaceutically acceptable salt.

A test was performed to demonstrate the activity of the kojic acid derivative having formula (I) according to the invention as a tyrosinase inhibitor by evaluating its effect on the dopa-oxidase activity of human melanocyte tyrosinase.

Human melanocytes were prepared and cultured and then introduced into media containing different concentrations of the kojic acid derivative having formula (I) according to the invention (0.1 mM, 0.2 mM, 0.3 mM and 0.6 mM).

After three days, the melanocytes were "trypsinized" in a mixture of trypsin/0.05% EDTA/0.02% in a phosphate buffer (50 mM at pH 6.8), washed three times in phosphate buffer containing 1% (w/v) Triton X-100 and subjected to ultrasound. After centrifugation, samples were taken and mixed with 5 mM L-dopa in phosphate buffer. The tyrosinase activity was evaluated by spectrophotometry by measuring the increase in the absorbance at 475 nm due to the formation of dopachrome from 5 mM dopa. The absorbance was read on a microplate reader at 25° C. for 60 minutes.

The activity of the cellular tyrosinase is measured relative to a standard range prepared with commercial tyrosinase.

The value of $IC_{50}$, i.e., the concentration of active product required to obtain a 50% inhibition of the production of melanin, is determined. For 5-hydroxy-4-oxo-4H-pyran-2-ylmethyl 2-oxothiazolidine-4-carboxylate of the present invention, this $IC_{50}$ value is from 0.2 to 0.3 mM, whereas it is from 1 to 2 mM for kojic acid.

Consequently, the kojic acid derivative having formula I according to the invention is more active than kojic acid in inhibiting tyrosinase activity and in inhibiting the production of melanin.

Preferably, the novel compound is a mixture of D- and L-isomers of 5-hydroxy-4-oxo-4H-pyran-2-yl methyl 2-oxothiazolidine-4-carboxylate having the formula (I). The D- and L-isomers may be prepared as the pure compounds, or as an enantiomeric mixture, which may be subsequently resolved and purified by conventional techniques.

According to a preferred embodiment of the invention, the composition contains a physiologically acceptable medium, that is to say one which is compatible with the skin, the scalp and the hair, and more particularly includes a cosmetic and/or dermatological, in particular bleaching and/or depigmenting, composition for topical application.

Preferably, the 5-hydroxy-4-oxo-4H-pyran-2-ylmethyl 2-oxothiazolidine-4-carboxylate or its salt may be present in the composition according to the invention in an amount ranging from 0.01 to 10% by weight and preferably from 0.1 to 5% of the total weight of the composition; and more preferably 0.1 to 2.5%. These ranges include all subranges and values in therebetween.

Preferably, any known suitable pharmaceutically acceptable salts may be used with the derivative of kojic acid of formula (I), according to the invention, including conventional non-toxic salts which include a metal salt such as an alkali metal salt (e.g. sodium salt, potassium salt, etc.) or an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N, N'-dibenzylethylenediamine salt, etc.), an organic acid salt (e.g. formate, acetate, trifluoroacetate, maleate, tartrate, methanesulfonate, benzenesulfonate, toluenesulfonate, etc.), an inorganic acid salt (e.g. hydrochloride, hydrobromide, sulfate, phosphate, etc.), a salt with an amino acid (e.g. arginine salt, aspartic acid salt, glutamic acid salt, methionine salt, etc.), and the like.

More preferably, the pharmaceutically acceptable salts may be obtained by reacting the compound of formula (I) with inorganic or organic acids or bases, such as hydrochloric acid, acetic acid, sodium hydroxide or triethanolamine.

Preferably, the composition of the invention may be in any pharmaceutical form or in any physiologically acceptable medium normally used for topical application, in particular in the form of an aqueous, aqueous-alcoholic or oily solution, an oil-in-water or water-in-oil or multiple emulsion, an aqueous or oily gel, a liquid, pasty or solid anhydrous product, a dispersion of oil in an aqueous phase with the aid of spherules, these spherules preferably being polymer nanoparticles such as nanospheres and nanocapsules or more preferably lipid vesicles of the ionic and/or nonionic type.

Preferably the composition according to the invention may be relatively fluid and have the appearance of a white or colored cream, an ointment, a milk, a lotion, a serum, a paste or a foam. It may optionally be applied to the skin in aerosol form. It may also be in solid form, for example, in the form of a stick. It may be used as a care product and/or as a make-up product.

Preferably the composition according to the invention may include any ingredient conventionally used in the cosmetic or dermatological field, in the usual concentrations. These ingredients are chosen in particular from fatty substances, preserving agents, vitamins, gelling agents, fragrances, surfactants, water, antioxidants, fillers, wetting agents, screening agents and mixtures thereof.

As fatty substances which may preferably be used in the invention, mention may be made of mineral oils (liquid petrolatum), oils of plant origin (jojoba oil), oils of animal origin, synthetic oils (isopropyl palmitate), silicone oils (cyclopentadimethylsiloxane) and fluoro oils. Fatty alcohols (stearyl alcohol), fatty acids and waxes may also be used.

As surfactants which may preferably be used in the invention, mention may be made, for example, of fatty acid esters of polyethylene glycol, such as poly-ethylene glycol stearate, and fatty acid esters such as sodium stearate.

EXAMPLES

Having generally described this invention, a further understanding can be obtained by reference to certain specific examples which are provided herein for purposes of illustration only and are not intended to be limiting unless otherwise specified. Concentrations are given as weight percent.

Example 1: Bleaching Cream for the Face

| | |
|---|---|
| 5-hydroxy-4-oxo-4H-pyran-2-ylmethyl 2-oxothiazolidine-4-carboxylate | 1% |
| sodium stearate | 3% |
| liquid petrolatum | 6% |
| preserving agent | 1% |
| cyclopentadimethylsiloxane | 2% |
| stearyl alcohol | 1% |
| fragrance | 1% |
| water | qs 100% |

When applied daily, the cream effectively bleaches the skin.

Example 2: Bleaching Cream for the Body

| | |
|---|---|
| 5-hydroxy-4-oxo-4H-pyran-2-ylmethyl 2-oxothiazolidine-4-carboxylate | 2.5% |
| jojoba oil | 13% |
| sipol wax | 6% |
| isopropyl palmitate | 2% |
| polyethylene glycol stearate | 3% |
| glycerol (wetting agent) | 15% |
| preserving agent | 0.5% |
| fragrance | 1% |
| water | qs 100% |

The cream obtained may be used daily and is exceptionally effective for depigmenting the skin.

Obviously, numerous modifications and variations of the present invention are possible in light of the above teachings. It is therefore to be understood that within the scope of the appended claims, the invention may be practiced otherwise than as specifically described herein.

This application is based on French Patent Application FR 96-09011, filed Jul. 18, 1996, the entire contents of which are hereby incorporated by reference.

What is claimed as new and desired to be secured by Letters Patent of the United States is:

1. A 5-hydroxy-4-oxo-4H-pyran-2-ylmethyl 2-oxothiazolidine-4-carboxylate compound having the formula (I):

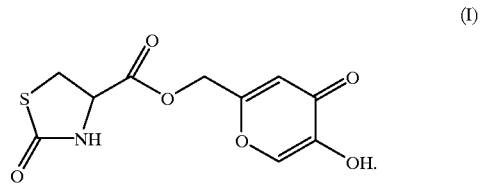

2. A composition, comprising:

a skin depigmenting effective amount of a 5-hydroxy-4-oxo-4H-pyran-2-ylmethyl 2-oxothiazolidine-4-carboxylate compound having the formula (I):

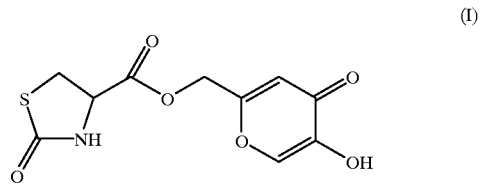

or pharmaceutically acceptable salts thereof and a physiologically acceptable medium.

3. The composition according to claim 2, wherein the compound of formula (I) is present in an amount ranging from 0.01 to 10% by weight, based on the total weight of the composition.

4. The composition according to claim 2, further comprising at least one ingredient selected from the group consisting of fatty substances, preserving agents, vitamins, gelling agents, fragrances, surfactants, water, antioxidants, fillers, screening agents, wetting agents and mixtures thereof.

5. The composition according to claim 4, wherein said fatty substance is an oil or wax.

6. The composition according to claim 4, wherein said surfactant is sodium stearate, polyethylene glycol stearate, or a mixture thereof.

7. The composition according to claim 2, wherein said skin is human skin.

8. A method of depigmenting skin, comprising:

applying, to skin, a composition containing a skin depigmenting effective amount of a 5-hydroxy-4-oxo-4H-pyran-2-ylmethyl 2-oxothiazolidine-4-carboxylate compound having the formula (I):

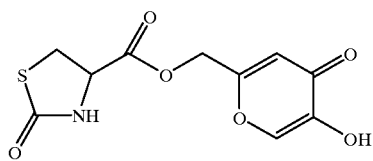

or a pharmaceutically acceptable salt thereof.

9. The method according to claim 8, wherein said skin is human skin.

10. A method of inhibiting the production of melanin, comprising:

contacting melanocytes with a melanin production inhibiting effective amount of a 5-hydroxy-4-oxo-4H-pyran-2-ylmethyl 2-oxothiazolidine-4-carboxylate compound having the formula (I):

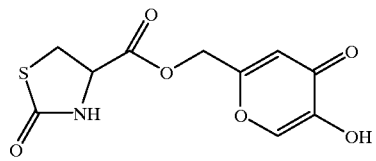

or a pharmaceutically acceptable salt thereof.

11. The method according to claim 10, where in said melanocytes are human melanoctyes.

* * * * *